United States Patent [19]

Eckstein et al.

[11] 4,140,852

[45] Feb. 20, 1979

[54] TRIAZINYL STYRYL-BENZOXAZOLE FLUORESCENT DYESTUFFS

[75] Inventors: Udo Eckstein, Cologne; Horst Harnisch, Much, both of Fed. Rep. of Germany

[73] Assignee: Bayer Aktiengesellschaft, Leverkusen, Fed. Rep. of Germany

[21] Appl. No.: 845,949

[22] Filed: Oct. 27, 1977

[30] Foreign Application Priority Data

Nov. 4, 1976 [DE] Fed. Rep. of Germany ....... 2650456

[51] Int. Cl.² .......................................... C07D 413/10
[52] U.S. Cl. .................................. 542/456; 542/431; 542/435
[58] Field of Search ...................... 252/301.23, 301.25; 542/456, 431, 435

[56] References Cited

U.S. PATENT DOCUMENTS

| | | | |
|---|---|---|---|
| 2,901,476 | 8/1959 | Gold et al. | 252/301.22 X |
| 3,684,729 | 8/1972 | Tuite | 252/301.23 |
| 3,689,481 | 9/1972 | Scheuermann et al. | 542/456 |
| 3,817,991 | 6/1974 | Meyer et al. | 252/301.23 X |
| 3,873,531 | 3/1975 | Elam | 542/456 |
| 4,008,172 | 2/1977 | von Rütte | 252/301.23 X |
| 4,066,830 | 1/1978 | Kormány | 542/456 |

FOREIGN PATENT DOCUMENTS 467391 6/1968 Japan ........................................ 542/456
996240 6/1965 United Kingdom ................ 252/301.23

*Primary Examiner*—Allen B. Curtis
*Attorney, Agent, or Firm*—Plumley and Tyner

[57] ABSTRACT

Fluorescent dyestuffs of the general formula wherein
X denotes O, S or N—$R_1$,
Y and Z denote halogen, hydroxyl, amino, alkoxy, aralkoxy, cycloalkoxy, aryloxy, alkylmercapto, arylmercapto, alkylamino, dialkylamino, acylamino, alkyl or aryl and
$R_1$ denotes hydrogen, alkyl, aralkyl, aryl or acyl, and the rings A and B and the cyclic and acyclic radicals $R_1$, Y and Z can carry non-chromophoric substituents which are customary for whiteners. and
the ring A, furthermore, can be fused to 1 or 2 carbocyclic, partially saturated or aromatic rings,
are suitable for the whitening of synthetic, semi-synthetic and natural organic high-molecular materials.

4 Claims, No Drawings

TRIAZINYL STYRYL-BENZOXAZOLE FLUORESCENT DYESTUFFS

The invention relates to fluorescent dyestuffs, processes for their preparation and their use for whitening organic materials.

The new compounds correspond to the formula

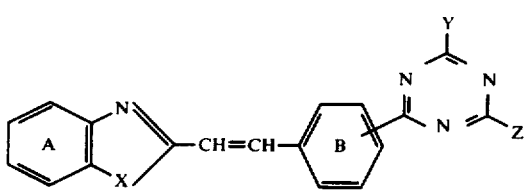

wherein

X denotes O, S or N—$R_1$,

Y and Z denote halogen, hydroxyl, amino, alkoxy, aralkoxy, cycloalkoxy, aryloxy, alkylmercapto, arylmercapto, alkylamino, dialkylamino, acylamino, alkyl or aryl and $R_1$ denotes hydrogen, alkyl, aralkyl, aryl or acyl, and the rings A and B and the cyclic and acyclic radicals $R_1$, Y and Z can carry non-chromophoric substituents which are customary for whiteners and the ring A, furthermore, can be fused to 1 or 2 carbocyclic, partially saturated or aromatic rings.

Preferred compounds of the formula (I) correspond to the formula

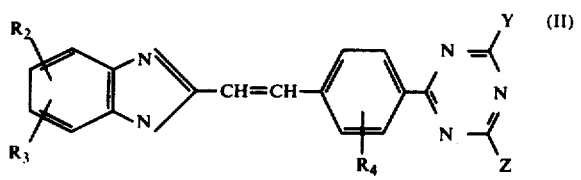

wherein

X, Y, Z and $R_1$ have the meaning indicated, $R_2$ and $R_3$ denote hydrogen, halogen, carboxyl, cyano, sulpho or an optionally substituted alkoxy, alkyl, cycloalkyl, aralkyl, aryl, alkoxycarbonyl, alkylsulphonyl, aminosulphonyl or carboxamide radical, or together in adjacent positions represent the remaining members of a partially saturated or aromatic fused hydrocarbon ring, and $R_4$ denotes hydrogen, halogen, cyano, sulpho, carboxyl or optionally substituted alkoxycarbonyl, alkoxy or alkyl.

Suitable halogen Y, Z, $R_2$, $R_3$ and $R_4$ is, for example, fluorine, chlorine and bromine, especially chlorine.

Suitable alkyl Y, Z, $R_1$, $R_2$, $R_3$ and $R_4$ is, in particular, alkyl with 1 to 4 C atoms, which can be monosubstituted by hydroxyl, $C_1$-$C_4$-alkoxy, cyano, carboxyl, $C_1$-$C_4$-alkoxycarbonyl, aminocarbonyl, chlorine or bromine, or trifluoromethyl.

Suitable cycloalkyl $R_2$ and $R_3$ is, in particular, cyclopentyl and cyclohexyl.

Suitable aralkyl $R_1$, $R_2$ and $R_3$ is, for example, phenyl-$C_1$-$C_4$-alkyl, which can be further substituted in the phenyl nucleus by chlorine, methyl, methoxy or sulpho.

Suitable aryl Y, Z, $R_1$, $R_2$ and $R_3$ is, in particular, phenyl which is optionally substituted by $C_1$-$C_4$-alkyl, trifluoromethyl, chlorine, bromine, $C_1$-$C_4$-alkoxy or sulpho.

Suitable alkoxy Y, Z, $R_2$, $R_3$ and $R_4$ is, in particular, —$(OCH_2CH_2)_m$—OR, R representing hydrogen or $C_1$-$C_4$-alkyl and m representing an integer from 0 to 20, with the proviso that R denotes alkyl when m is 0.

Suitable cycloalkoxy Y and Z is, in particular, cyclopentyloxy and cyclohexyloxy.

Suitable aralkoxy Y and Z is, in particular, benzyloxy and 2-phenethyloxy.

Suitable aryloxy Y and Z is, in particular, phenoxy which is optionally substituted by methyl, methoxy, chlorine or sulpho.

The alkyl radicals in alkylamino Y and Z, in dialkylamino Y and Z, in alkylmercapto Y and Z and in alkylsulphonyl $R_2$ and $R_3$ are, in particular, $C_1$-$C_4$-alkyl which is not further substituted, it being possible for the dialkylamino groups also to be cyclised to form piperidine, piperazine, morpholine and pyrrolidine rings.

Arylmercapto is, in particular, phenylmercapto which is optionally substituted by methyl, methoxy, chlorine or sulpho.

Acyl radicals $R_1$ and acyl radicals in acylamino for Y and Z are, in particular, $C_1$-$C_4$-alkylcarbonyl, $C_1$-$C_4$-alkylsulphonyl and benzoyl or benzenesulphonyl which is optionally substituted by methyl, methoxy, chlorine or sulpho.

The alkoxy groups of the alkoxycarbonyl radicals $R_2$, $R_3$ and $R_4$ contain, in particular, 1 to 4 C atoms.

The carboxamide and aminosulphonyl groups $R_2$ and $R_3$ can be substituted by $C_1$-$C_4$-alkyl, benzyl, 2-phenethyl and phenyl which is optionally further substituted by methyl, methoxy, chlorine or sulpho.

Fused rings, which $R_2$ and $R_3$ form together, are, in particular, 1-cyclopentene, 1-cyclohexene or benzene rings which are optionally substituted by 1 or 4 methyl groups.

Particularly preferred compounds correspond to the formula

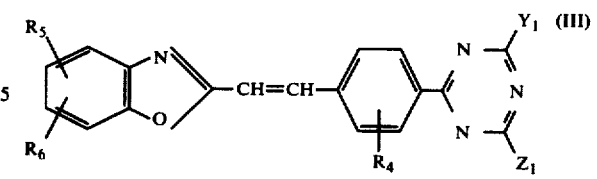

wherein $R_5$ denotes hydrogen, chlorine, $C_1$-$C_4$-alkyl, phenyl-$C_1$-$C_3$-alkyl, cyclohexyl, phenyl, $C_1$-$C_4$-alkoxy, $C_1$-$C_4$-alkylsulphonyl, $C_1$-$C_4$-alkoxycarbonyl, cyano or carboxyl, $R_6$ denotes hydrogen, chlorine or methyl or, together with $R_5$, a fused 1-cyclopentene, 1-cyclohexene or benzene ring which is optionally substituted by 1 to 4 methyl groups, $Y_1$ denotes chlorine, —$(OCH_2CH_2)_p$—$OR_7$, $C_1$-$C_4$-alkylamino, di-$C_1$-$C_4$-alkylamino, morpholino, piperidino or phenylamino, $Z_1$ denotes chlorine or —$(OCH_2CH_2)_p$—$OR_7$, $R_7$ denotes hydrogen, $C_1$-$C_4$-alkyl, benzyl or phenyl and p denotes an integer from 0 to 7.

Particularly valuable compounds of the formula (III) are those in which $Y_1$ and $Z_1$ has the meaning —$(OCH_2CH_2)_q$—$OR_8$, q representing an integer from 0 to 2 and $R_8$ denoting $C_1$-$C_4$-alkyl.

Amongst these, those in which $R_6$ denotes hydrogen and the radical $R_5$ is in the 5-position of the benzoxazolyl ring are, in turn, preferred.

The benzoxazolyl compounds according to the invention can be prepared by various processes which are in themselves known.

1st Process

Phosphono compounds of the formula

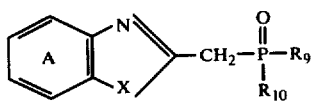
(IV)

wherein

X and A have the meaning given above and $R_9$ and $R_{10}$ represent $C_1$-$C_4$-alkoxy, $C_5$-$C_6$-cycloalkoxy or phenoxy, are subjected to a condensation reaction with benzaldehydes of the formula

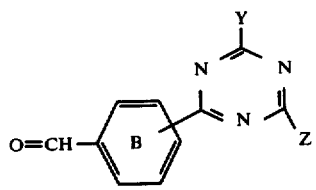
(V)

wherein

B, Y and Z have the meaning given above, in organic solvents in the presence of basic condensing agents.

Inert solvents are preferably chosen as the solvent, for example hydrocarbons, such as toluene or xylene, or alcohols, such as methanol, ethanol, isopropanol, butanol, glycol or glycol ethers, such as 2-methoxyethanol; hexanol, cyclohexanol or cyclooctanol, and also ethers, such as diisopropyl ether, dioxane or tetrahydrofurane, and furthermore formamides or N-methylpyrrolidone. Dipolar organic solvents, such as dimethylformamide and dimethylsulphoxide, are particularly suitable.

Condensing agents which can be used are strongly basic compounds, such as alkali metal hydroxides or alkaline earth metal hydroxides, alkali metal amides or alkaline earth metal amides and alkali metal alcoholates or alkaline earth metal alcoholates, for example potassium hydroxide, sodium hydroxide, potassium tert.-butylate, sodium amide or sodium methylate, and also the alkali metal compounds of dimethylsulphoxide and alkali metal hydrides, as well as, in some cases, alkali metal dispersions.

The reaction is preferably carried out in the temperature range from 0°–100° C. The phosphono compounds (III) are obtained by reacting 2-halogenomethylbenzazoles with phosphorous acid trialkyl esters.

2nd Process

Aniline derivatives of the formula

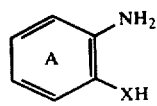
(VI)

wherein

A and X have the meaning given above, are reacted with functional derivatives, in particular the acid halides, of cinnamic acids of the formula

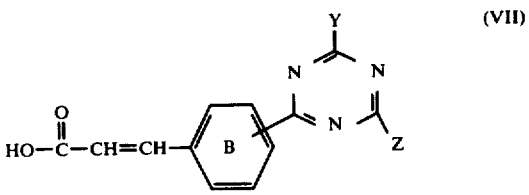
(VII)

wherein

Y, Z and B have the meaning given above, to give the corresponding acylamino compounds and these compounds are cyclised in the presence of acid catalysts to form the azoles.

The acylation is effected in inert solvents, preferably in the presence of acid acceptors, in particular tertiary organic bases, such as triethylamine, dimethylaniline, pyridine, dimethylaniline or hexahydrodimethylaniline, at temperatures between 20° and 140° C., preferably 60° to 130° C.

Inert solvents which can be used are, for example, ethers, such as dioxane, tetrahydrofurane, diisopropyl ether, glycol ethers and 2-methoxyethanol, and also hydrocarbons, such as toluene, xylene, chlorobenzene and 1,2-dichlorobenzene, and formamides, such as dimethylformamide.

The acylamino compounds are cyclised, with the splitting-off of water, in inert organic solvents, such as o-dichlorobenzene, 1,2,4-trichlorobenzene, trichlorobenzene mixtures, α-chloronaphthalene or benzoic acid methyl ester, in the presence of catalytic amounts of acid catalysts, such as paratoluenesulphonic acid, zinc chloride, polyphosphoric acid or boric acid, at temperatures from about 180° to 260° C., preferably 200° to 250° C.

3rd Process

Benzaldehydes of the formula (IV) are subjected to a condensation reaction with 2-methylazoles of the formula

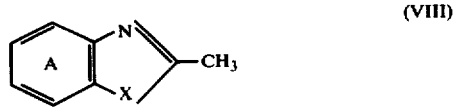
(VIII)

in which

A and X have the meaning given above, at elevated temperature in an inert solvent and in the presence of an agent which splits off water, preferably under acid catalysis. The water formed during the condensation reaction is appropriately removed from the reaction mixture by azeotropic distillation.

The products obtained by processes 1 to 3 can, of course, be still further altered by processes which are in themselves known, for example by halogenation reactions, functional modifications of carboxyl groups, introduction of chloromethyl groups or replacement of halogen atoms by cyano groups.

Because of their absorption in the ultraviolet region and their fluoroescence, the compounds according to the invention are suitable for whitening the most diverse synthetic, semi-synthetic and natural organic high-molecular materials, such as are given in detail in the following.

I.

Synthetic organic high-molecular materials:

a. Polymerisation products based on organic compounds containing at least one polymerisable carbon-carbon double bond, that is to say their homopolymers or copolymers as well as their after-treatment products, such as, for example, cross-linking, grafting or degradation products, polymer blends and the like, of which the following may be mentioned as examples: polymers based on $\alpha,\beta$-unsaturated carboxylic acids, especially on acrylic compounds (such as, for example, acrylic esters, acrylic acids, acrylonitrile, acrylamides and their derivatives or their methacrylic analogues) and an olefine hydrocarbons (such as, for example, ethylene, propylene, isobutylene, styrenes and dienes, such as, in particular, butadiene and isoprene, that is to say, thus, also rubbers and rubber-like polymers, and also so-called ABS polymers), polymers based on vinyl and vinylidene compounds (such as, for example, vinyl esters, vinyl chloride, vinylsulphonic acid, vinyl ether, vinyl alcohol, vinylidene chloride and vinylcarbazole), on halogenated hydrocarbons (chloroprene and post-halogenated ethylenes), on unsaturated aldehydes and ketones (for example acrolein and the like) and on allyl compounds and the like, graft polymerisation products (for example those obtained by the grafting on of vinyl monomers), crosslinked products (for example those obtained by means of bifunctional or polyfunctional crosslinking agents, such as divinylbenzene, polyfunctional allyl compounds or bisacrylic compounds) or are obtained by partial degradation (hydrolysis or depolymerisation) or modification of reactive groupings (for example esterification, halogenation or spontaneous crosslinking).

b. Other polymerisation products, such as are obtainable, for example, by ring opening, for example polyamides of the polycaprolactam type, and also formaldehyde polymers or polymers which are obtainable both via polyaddition and via polycondensation, such as polyethers, polythioethers, polyacetals or thioplasts.

c. Polycondensation products or precondensates based on bifunctional or polyfunctional compounds having condensable groups, their homocondensation and co-condensation products as well as after-treatment products, of which the following may be mentioned as examples: polyesters, that is to say polyesters which are saturated (for example polyethylene terephthalate) or unsaturated (for example maleic acid/dialcohol polycondensates as well as their crosslinking products with copolymerisable vinyl monomers), unbranched or branched (also those based on polyhydric alcohols, such as, for example, alkyd resins); and polyamides (for example hexamethylenediamine adipate), maleate resins, melamine resins, phenolic resins, aniline resins, furane resins, carbamide resins and also their precondensates and products of analogous structure, polycarbonates, silicone resins and others.

d. Polyaddition products, such as polyurethanes (crosslinked and non-crosslinked) and epoxide resins.

II.

Semi-synthetic organic materials, such as, for example, cellulose esters or mixed esters (acetate or propionate), nitro-cellulose, cellulose ethers, regenerated cellulose (viscose or copper ammonium cellulose), or their after-treatment products, and casein plastics.

III.

Natural organic materials of animal or vegetable origin, for example based on cellulose or proteins, such as wool, cotton, silk, bast, jute, hemp, skins and hairs, leather, finely divided wood compositions, natural resins (such as colophonium and in particular lacquer resins), and also rubber, guttapercha and balata, as well as their after-treatment and modification products (for example those obtained by curing, crosslinking or grafting), degradation products (for example those obtained by hydrolysis or depolymerisation) and those products obtainable by modifying reactive groups (for example by acylation, halogenation, crosslinking and the like).

The organic materials which can be used can be in the most diverse states of processing (raw materials, semifinished goods or finished goods) and states of aggregation. On the one hand, they can be in the form of structures of the most diverse shapes, that is to say, thus, for example predominantly three-dimensional bodies, such as blocks, slabs, profiles, tubes, injection mouldings or the most diverse machined articles, chips or granules or foams, and also predominantly two-dimensional bodies, such as films, sheets, lacquers, tapes, coverings, impregnations and coatings, or predominantly one-dimensional bodies, such as filaments, fibres, flocks, bristles and wires. The said materials can, on the other hand, also be in unshaped states in the most diverse homogeneous and inhomogeneous forms of division and states of aggregation, for example in the form of powders, solutions, emulsions, dispersions and latices (examples: lacquer solutions, polymer dispersions, sols, jellies, putties, pastes, waxes, adhesive compositions and trowelling compounds, and the like).

Fibre materials can, for example, be in the form of continuous filaments, staple fibres, flocks, hanks, textile filaments, yarns, threads, fibre fleeces, felts, waddings, flocked structures or woven textile fabrics or textile laminates, knitted fabrics and papers, cardboards or paper pulps and the like.

The compounds to be used according to the invention are also of importance for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be whitened according to the invention, this is advantageously effected in an aqueous medium, wherein the compounds concerned are present in a finely divided form (suspensions or, in some cases, solutions). If appropriate, dispersing agents can be added during the treatment, such as, for example, soaps, polyglycol ethers of fatty alcohols, fatty amines or alkylphenols, cellulose sulphite waste liquors or condensation products of optionally alkylated naphthalenesulphonic acids and formaldehyde. It proves particularly advantageous to carry out the treatment in a neutral, weakly alkaline or acid bath. It is also advantageous if the treatment is effected at elevated temperatures of about 50° to 100° C., for example at the boiling point of the bath or near it (about 90° C.). Solutions in organic solvents can also be used for the finishing according to the invention, as is practiced in the dyeing trade in so-called solvent dyeing (pad-thermofix application or the exhaustion dyeing process in drum dyeing machines), for example for polyamide and polyester substrates.

The new whiteners to be used according to the invention can further be added to, or incorporated in, the materials before or during their shaping. Thus, for example, they can be added to the compression moulding composition or injection moulding composition during the production of films, sheets, tapes or shaped articles, or they can be dissolved or dispersed, or otherwise homogeneously finely distributed, in the spinning compositions before spinning. The whiteners can also be added to the starting materials, reaction mixtures or intermediate products for the preparation of fully synthetic or semi-synthetic organic materials, that is to say also before or during the chemical reaction, for example in the case of a polycondensation reaction (that is to say also to the precondensates), in the case of a polymerisation reaction (that is to say also to the prepolymers) or a polyaddition reaction.

The new whiteners can, of course, also be employed in all cases where organic materials of the type indicated above are combined with inorganic materials in any form (typical examples: washing agents or white pigments in organic substances).

The new whitening substances are distinguished by a particularly good resistance to heat, fastness to light and resistance to migration.

The amount of the new whitener to be used according to the invention, relative to the material to be whitened, can vary within wide limits. A distinct and durable effect is already achieved with very small amounts, in certain cases, for example amounts of 0.001% by weight. However, amounts of up to about 0.5% by weight and more can be used. For most practical purposes, amounts between 0.01 and 0.2% by weight are preferably of interest.

The new compounds, which are used as whiteners, can also be employed, for example, as follows:

a. Mixed with dyestuffs or pigments or as additives to dyebaths, printing pastes, discharge pastes or reserve pastes. Furthermore, also, for the after-treatment of dyeings, prints or discharge prints.

b. Mixed with so-called "carriers", antioxidants, light stabilisers, heat stabilisers and chemical bleaching agents or as an additive to bleaching baths.

c. Mixed with crosslinking agents or finishing agents, such as starch or synthetically accessible finishes. The products according to the invention can also advantageously be added to the liquors used for achieving a creaseproof finish.

d. In combination with washing agents. The washing agent and brightener can be added separately to the wash baths which are to be used. It is also advantageous to use washing agents which contain the whiteners as an admixture. Suitable washing agents are, for example, soaps, salts of sulphonate washing agents, such as, for example, of sulphonated benzimidazoles which are substituted on the 2-carbon atom by higher alkyl radicals, and also salts of monocarboxylic acid esters of 4-sulphophthalic acid with higher fatty alcohols, and furthermore salts of fatty alcohol sulphonates, alkylarylsulphonic acids or condensation products of higher fatty acids with aliphatic hydroxysulphonic or aminosulphonic acids. Non-ionic washing agents can also be used, for example polyglycol ethers which are derived from ethylene oxide and higher fatty alcohols, alkylphenols or fatty amines.

e. In combination with polymeric carriers (polymerisation, polycondensation or polyaddition products), in which the whiteners are incorporated, optionally in addition to other substances, in the dissolved or dispersed form, for example in the case of coating agents, impregnating agents or binding agents (solutions, dispersions, emulsions), textiles, fleeces, paper or leather.

f. As additives to the most diverse industrial products in order to render these more marketable or to avoid disadvantages in their usability, for example as an additive to sizes, adhesives, toothpastes, paints and the like.

g. In combination with other substances having a whitening action (for example for the purpose of altering the shade).

h. In spinning bath preparations, that is to say as additives to spinning baths such as are used for improving the slip for the further processing of synthetic fibres.

The compounds of the formula initially indicated can be used as scintillators for various purposes of a photographic nature, such as for electrophotographic reproduction or for supersensitisation.

If the whitening process is combined with other treatment or finishing methods, the combined treatment is advantageously effected with the aid of corresponding stable formulations. Such formulations are characterised in that they contain the whitening compounds of the general formula initially indicated, as well as dispersing agents, washing agents, carriers, dye-stuffs, pigments or finishing agents.

In the treatment of a range of fibre substrates, for example polyester fibres, with the whiteners according to the invention, the procedure followed is appropriately to impregnate these fibres with the aqueous dispersions of the whiteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. up to about 100° C. The heat treatment in the dry state is then advantageously carried out at temperatures between 120° and 225° C., for example by warming in a drying chamber, by ironing in the temperature range indicated or also by treatment with dry, superheated steam. The drying and dry heat treatment can also be carried out in immediate succession or be combined in a single operation.

EXAMPLE 1

20 g. (0.11 mol) of 2-chloromethyl-5-methylbenzoxazole, 75 g (0.6 mol) of trimethyl phosphite and 200 ml of dimethylformamide and heated to 130 to 140° C. for 4 hours. Thereafter, excess trimethyl phosphite and most of the dimethylformamide are distilled off in vacuo. The residue and 24.5 g (0.1 mol) of 4,6-dimethoxy-2-(4-formylphenyl)-1,3,5-triazine are dissolved in 200 ml of dimethylformamide and 12 g (0.22 mol) of sodium methylate are added in portions. After the suspension has been stirred under nitrogen for 4 hours at 50° C., the reaction mixture is discharged onto 500 ml of water and 100 ml of acetic acid are added. After cooling to 0° C., filtering off the precipitate and washing until neutral, 28.6 g (77% of theory) of the compound of the formula

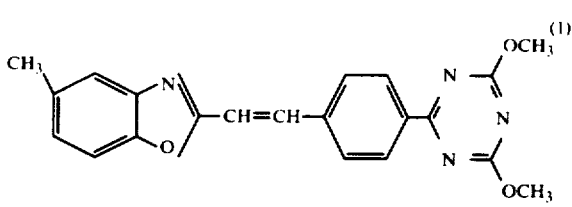

are obtained as a light yellow crystalline powder, which is purified by recrystallisation from toluene. The substance exhibits a deep blue fluorescence when dissolved in dimethylformamide and has, when incorporated into polyester, a strong brightening effect with good fastness properties.

The aldehyde of the formula

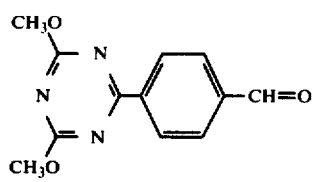

which is used as prepared in the following manner:

A mixture of 18.2 g (0.1 mol) of N-bromosuccinimide and 0.2 g of azoisobutyronitrile is added in portions to a solution of 23.1 g (0.1 mol) of 4,6-dimethoxy-2-(4-methylphenyl)-1,3,5-triazine and 0.1 g of dibenzoyl peroxide in 200 ml of anhydrous carbon tetrachloride at 60° C. in the course of 20 minutes and the mixture is stirred at the reflux temperature for 4 hours. Thereafter, the succinimide is filtered off at 60° C., the filter cake is rinsed with hot carbon tetrachloride (about 50 to 100 ml) and the filtrate is evaporated almost to dryness. The residue is filtered off and washed with petroleum ether (40 to 80° C.). 27.6 g (89% of theory) of the bromomethyl compound of melting point 146° C. are thus obtained, which, when recrystallised from ethyl acetate, gives colourless crystals of melting point 154° C.

31 g (0.1 mol) of crude 4,6-dimethoxy-2-(4-bromomethylphenyl)-1,3,5-triazine are boiled with 15.5 g (0.11 mol) of hexamethylenetetramine in 100 ml of chloroform for 4 hours under reflux. Thereafter, 50 ml of chloroform are distilled off, the mixture is cooled and 50 ml of acetone are added. After filtering, 40.2 g of the urotropine salt are obtained, which is heated in 100 ml of 50% strength acetic acid for 2 hours under reflux. The pH of the solution is adjusted to 3 with about 10 to 20 ml of concentrated hydrochloric acid and, after boiling up briefly, the mixture is cooled to 0° C., and 500 ml of water are added. The precipitate which has separated out is filtered off and washed with water until neutral. This gives 15 g (61.2% of theory) of colourless crystals of melting point 136°-138° C., which, when recrystal-lised from methylglycol, give colourless needles of melting point 149°-150° C.

The aldehyde of the formula (3) is also prepared analogously.

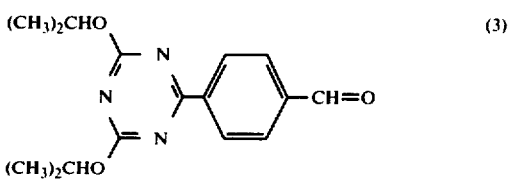

Yield: 71.7% of theory, melting point: 109° C.

EXAMPLE 2

Analogously to Example 1, the reaction of (2) with the phosphono derivative obtained from 18.4 g (0.11 mol) of 2-chloromethylbenzoxazole gives 27.3 g (76% of theory) of the compound of the formula

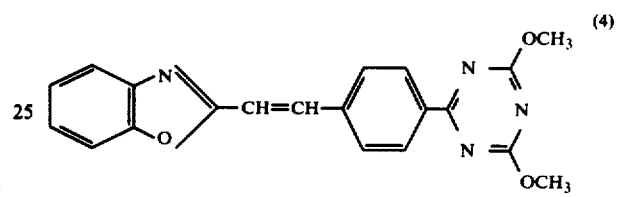

as yellow crystals. They can be purified by recrystallising from dimethylformamide with the addition of active charcoal. Fluorescence in dimethylformamide: blue.

EXAMPLE 3

In a similar manner to that in Example 1, 20 g (0.12 mol) of 2-chloromethylbenzoxazole gives the corresponding phosphono compound which gives, when subjected to a condensation reaction with 30.1 g (0.1 mol) of 4,6-diiso-propyloxy-2-(4-formylphenyl)-1,3,5-triazine (3), the compound of the formula

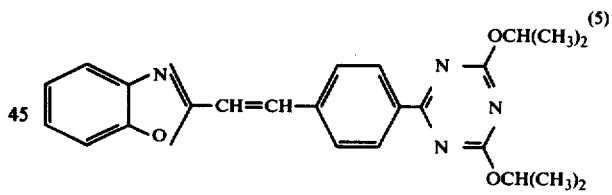

When recrystallised from toluene, pale yellow crystals are obtained, which, when dissolved in dimethylformamide and in chlorobenzene, exhibit an intensive, reddish-tinged blue fluorescence in UV light.

The compounds of the formula (6) to (27) listed in Table I which follows are prepared in an analogous manner. They possess valuable properties as whiteners.

Table I

| No. | $Q_1$ | $Q_2$ | $Q_3$ | Fluorescence colour in dimethylformamide |
|---|---|---|---|---|
| 6 | Chlorine | Methoxy | Chlorine | reddish-tinged blue |
| 7 | Methyl | Benzyloxy | Benzyloxy | blue |

Table I-continued

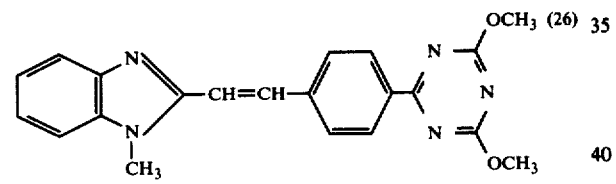

| No. | $Q_1$ | $Q_2$ | $Q_3$ | Fluorescence colour in dimethylformamide |
|---|---|---|---|---|
| 8 | tert.-Butyl | Ethoxy | Ethoxy | greenish-tinged blue |
| 9 | Benzyl | Chlorine | Methoxy | blue |
| 10 | 2-Phenylethyl | Methoxy | n-Butoxy | blue |
| 11 | 2-Phenyl-isopropyl | 2-Methoxyethoxy | 2-Methoxyethoxy | reddish-tinged blue |
| 12 | Cyclohexyl | 2-n-Butoxyethoxy | 2-n-Butoxyethoxy | reddish-tinged blue |
| 13 | Phenyl | Diethylamino | Chlorine | blue |
| 14 | Methoxy | $(OC_2H_4)_7$—$OCH_3$ | Methoxy | reddish-tinged blue |
| 15 | Ethoxy | Chlorine | Ethoxy | blue |
| 16 | Methylsulphonyl | Methoxy | Phenoxy | blue |
| 17 | Ethylsulphonyl | Phenoxy | Phenoxy | blue |
| 18 | n-Butylsulphonyl | Methylamino | Methoxy | greenish-tinged blue |
| 19 | Methoxycarbonyl | Morpholinyl-(1) | Methoxy | greenish-tinged blue |
| 20 | Ethoxycarbonyl | 2-Ethoxyethoxy | 2-Ethoxyethoxy | reddish-tinged blue |
| 21 | n-Butoxycarbonyl | Anilino | Methoxy | greenish-tinged blue |
| 22 | Cyano | n-Butoxy | n-Butoxy | reddish-tinged blue |
| 23 | Carboxyl | 2-(Hydroxyethoxy)-ethoxy | 2-(2-Hydroxyethyl)-ethoxy | blue |
| 24 | Cyano | Pyrrolidino | Chlorine | blue |
| 25 | Methyl | Di-n-butylamino | Methoxy | reddish-tinged blue |

EXAMPLE 4

If 2-chloromethyl-5-methyl-benzoxazole in Example 1 is replaced by the equivalent amount of 1-methyl-2-chloromethylbenzimidazole, the compound of the formula

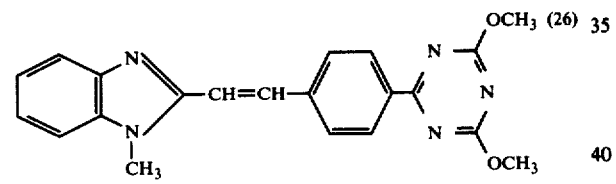

is obtained, which exhibits a deep blue fluorescence in dimethylformamide.

The compound (27) is correspondingly obtained from 1-phenyl-2-chloromethylbenzimidazole and 2-(4-formylphenyl)-4-methoxy-6-N-n-butylamino-1,3,5-triazine.

EXAMPLE 5

If 2-chloromethylbenzoxazole in Example 2 is replaced by the equivalent amount of 2-chloromethyl-naphtho-[1,2-d]-oxazole, the compound of the formula

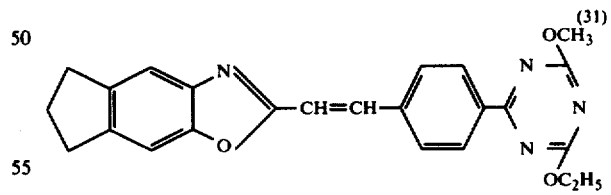

is obtained, which exhibits a blue fluorescence in dimethylformamide.

Compound (29) which exhibits a greenish-tinged blue fluorescence in dimethylformamide, is obtained from the same naphthoxazole with 2-(4-formylphenyl)-4-ethoxy-6-n-butylamino-1,3,5-triazine.

Analogously, 5,6,7,8-tetrahydro-2-chloromethyl-naphtho-[2,3-d]-oxazole and 2-(4-formylphenyl)-4-methoxy-6-dimethylamino-1,3,5-triazine give the compound (30), which exhibits a deep blue fluorescence.

The compounds of the formula

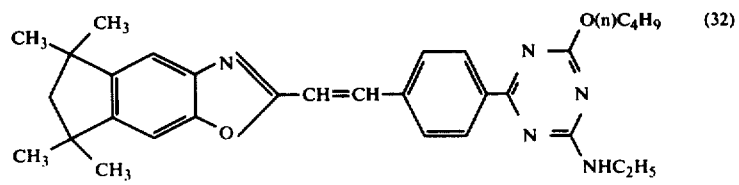

(blue fluorescence in dimethylformamide) and of the formula

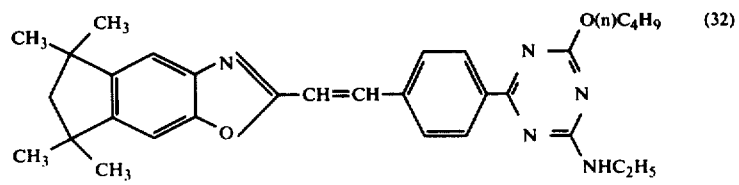

(greenish-tinged blue fluorescence in dimethylformamide) are obtained in an analogous manner from the corresponding starting compounds.

With 2-(4-formylphenyl)-4-piperidino-6-methoxy-1,3,5-triazine, 2-chloromethyl-5,6-dimethylbenzoxazole gives the compound (33), which exhibits a greenish-tinged blue fluorescence in dimethylformamide.

With 2-(4-formylphenyl)-4-methoxy-6-[2-(2-methoxyethoxy)ethoxy]-1,3,5-triazine, 2-chloromethyl-5,7-dichlorobenzoxazole gives the compound (34), which exhibits a strong blue fluorescence in dimethylformamide.

EXAMPLE 6

39.7 g (0.1 mol) of 4,6-di-(4-methoxyphenyl)-2-(4-formylphenyl)-1,3,5-triazine, 13.4 g (0.1 mol) of 2-methylbenzoxazole, 19 g (0.11 mol) of p-toluenesulphonic acid and 10 g (0.14 mol) of dimethylformamide are added to 300 ml of anhydrous xylene in a reflux apparatus which is provided with a water separator. The reaction mixture is heated to the boil in a nitrogen atmosphere, whilst stirring, until no more water is formed (about 20 to 30 hours). After distilling off most of the xylene, the mixture is cooled and 100 ml of 10% strength aqueous sodium carbonate solution are added. The mixture is then subjected to steam distillation. This gives 41.6 g (81.2% of theory) of the compound of the formula

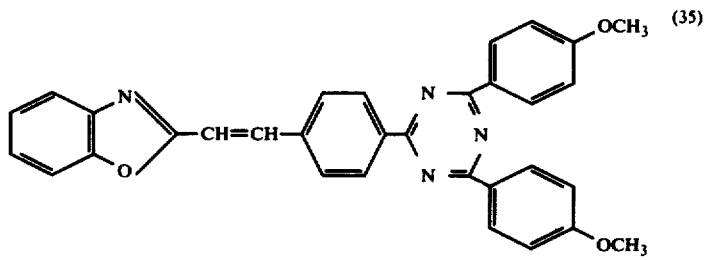

in light yellow crystals. Purification is effected by recrystallising from xylene. Fluorescence in dimethylformamide: blue.

The aldehyde of the formula

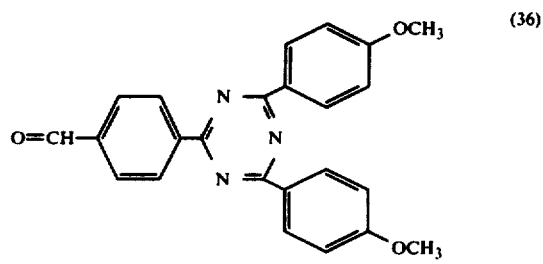

used can be synthesized, according to Example 1, from the corresponding tolyl compound by bromination with N-bromosuccinimide, subsequent reaction of the product with hexamethylenetetramine and decomposition of the quaternary ammonium salt. This gives yellowish crystals of melting point 179° C. (from n-butanol).

EXAMPLE 7

The compound of the formula

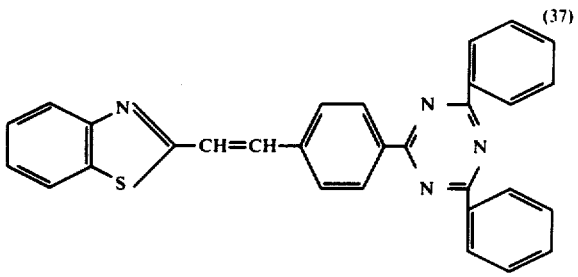

is obtained, by the process indicated in Example 4, from 16.4 g (0.11 mol) of 2-methylbenzthiazole and 34 g (0.1 mol) of 4,6-diphenyl-2-(4-formylphenyl)-1,3,5-triazine. Yield: 90% of theory. Recrystallisation from xylene gives a yellow crystalline powder which has a reddish-tinged blue fluorescence when dissolved in dimethylformamide.

EXAMPLE 8

33.7 g (0.1 mol) of crude 4,6-diphenyl-2-(4-formylphenyl)-1,3,5-triazine are heated with 100 ml of pyridine/1 g of piperidine and 11.4 g (0.11 mol) of malonic acid for 10 hours under reflux. The reaction mixture is stirred into 500 ml of water and 50 ml of concentrated hydrochloric acid and the crude cinnamic acid is isolated by filtering off and washing with water. After drying in vacuo, 34 g (89.7% of theory) of colourless crystals are obtained of melting point 260 to 262° C. (methylglycol or glacial acetic acid).

37.9 g (0.1 mol) of the compound described above are converted into the acid chloride with 15 g (0.12 mol) of thionyl chloride and 2 g of dimethylformamide in 100 ml of anhydrous toluene (about 2 hours reflux). A mixture of 14.7 g (0.1 mol) of 4-amino-5-hydroxy-1,2-xylene and 13 g (0.11 mol) of N,N-dimethylaniline in 80 ml of dioxane is then added dropwise under a nitrogen atmosphere at room temperature. After warming to 80° C. for five hours, the reaction mixture is freed from toluene by means of steam. The product which has separated out is filtered off, washed with dilute hydrochloric acid and water and, after drying in vacuo, is heated under nitrogen, with 0.5 g of boric acid in a mixture of 50 ml of distilled chlorobenzene and 150 ml of trichlorobenzene, to 160° C. for 3 hours and then to 205 to 210° C. for 1 hour, whereupon about 120 to 150 ml of solvent are distilled off azeotropically with the water formed. After cooling, the residue is allowed to crystallise, with the addition of 80 ml of methanol; yield: 41.1 g (86.2% of theory).

Recrystallisation from xylene gives, with the addition of bleaching earth, pale yellow crystals of the formula

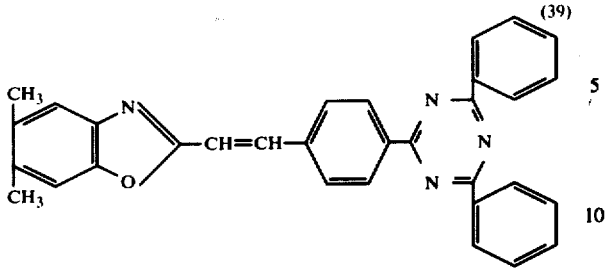

(39)

which, when dissolved in dimethylformamide, exhibit a deep blue fluorescence.

EXAMPLE 9

If the procedure followed is as indicated in Example 8 but 4-tert.-butyl-2-aminophenyl is used instead of 4-amino-5-hydroxy-1,2-xylene, the compound of the formula

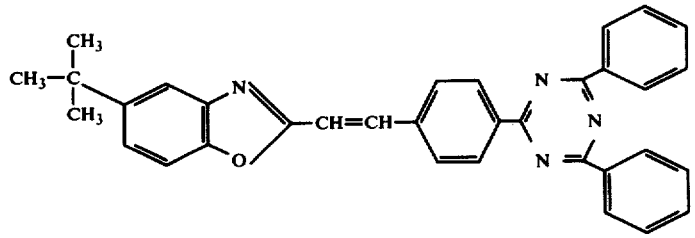

is obtained in 89% yield as pale yellow crystals which, when dissolved in dimethylformamide, exhibit blue fluorescence.

EXAMPLE 10

100 g of polyester granules of terephthalic acid and ethylene glycol are intimately mixed with 0.05 g of one of the compounds of the formula (1), (4) or (5) and the mixture is melted at 285° C., whilst stirring. After spinning through customary spinnerets, strongly brightened polyester fibres are obtained.

The compounds of the formula (1), (4) or (5) can also be added to the starting materials before or during the polycondensation.

EXAMPLE 11

A woven fabric consisting of polyethylene glycol terephthalate filaments is treated, in the ratio 1:20, in an aqueous liquor which contains 1 g/l of sodium chloride and, in the dispersed form, 0.05 g/l of one of the brighteners listed under No. 6, 8, 9, 13, 24 and 34 in Table I. The bath is brought to 125° C. in a high temperature (HT apparatus) for 45 minutes and the textile material is treated for a further 45 minutes at this temperature. After rinsing and drying, the woven fabric thus treated exhibits a very good whitening effect which is fast to light and which is substantially more brilliant than that which can be achieved by treatment with sodium chlorite by itself.

EXAMPLE 12

In a rotary autoclave, a woven fabric consisting of polyester fibres (polyethylene glycol terephthalate) is introduced, in a liquor ratio of 1:40, into a bath which contains, per liter, 1.5 g of sodium oleylsulphonate, 1 g of oxalic acid and 0.05 g of one of the compounds listed under 11 to 35 in the table. The rotary autoclave is kept at 125° C. for 45 minutes, under moderate agitation.

After cooling, the woven fabric is rinsed and dried; it exhibits a clear and attractive brightening of good fastness to light, washing and chlorite.

EXAMPLE 13

100 parts of polystyrene and 0.1 part of one of the compounds No. 11, 12, 15, 22, 23, 28 or 34 are melted for 20 minutes at 210° C. in a tube having a diameter of 1 cm, with the exclusion of air. After cooling, an optically brightened polystyrene composition of good fastness to light is obtained.

EXAMPLE 14

100 g of polypropylene "Fibre Grade" are intimately mixed with 0.8 g of one of the compounds No. 4, 5, 11, 13 or 21 to 25 and the mixture is melted at 280 to 290° C., whilst stirring. The melt is spun and drawn through customary spinnerets by melt spinning processes which are in themselves known. Strongly brightened polypropylene fibres are obtained.

We claim:

(40)

1. Fluorescent dyestuffs of the formula

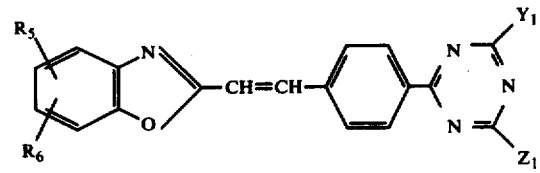

wherein
- $R_5$ denotes hydrogen, chlorine, $C_1-C_4$-alkyl, phenyl-$C_1-C_3$-alkyl, cyclohexyl, phenyl, $C_1-C_4$-alkoxy, $C_1-C_4$-alkylsulphonyl, $C_1-C_4$-alkoxycarbonyl, cyano or carboxyl,
- $R_6$ denotes hydrogen, chlorine or methyl or, together with $R_5$, a fused 1-cyclopentene, 1-cyclohexene or benzene ring which is optionally substituted by 1 to 4 methyl groups,
- $Y_1$ denotes chlorine, —$(OCH_2CH_2)_p$—$OR_7$, $C_1-C_4$-alkylamino, di-$C_1-C_4$-alkylamino, morpholino, piperidino or phenylamino,
- $Z_1$ denotes chlorine or —$(OCH_2CH_2)_p$—$OR_7$,
- $R_7$ denotes hydrogen, $C_1-C_4$-alkyl, benzyl or phenyl and p denotes an integer from 0 to 7.

2. Fluorescent dyestuffs according to claim 1, wherein $Y_1$ and $Z_1$ denote —$(OCH_2-CH_2)_q$—$OR_8$, q representing an integer from 0 to 2 and $R_8$ denoting $C_1-C_4$-alkyl.

3. Fluorescent dyestuffs according to claim 2, wherein $R_6$ denotes hydrogen and $R_5$ is in the 5-position of the benzoxazolyl ring.

4. Process for whitening synthetic, semi-synthetic and natural organic high-molecular materials, characterised in that fluorescent dyestuffs according to claim 1 are used.